(12) United States Patent
Kritzler

(10) Patent No.: US 8,524,799 B2
(45) Date of Patent: Sep. 3, 2013

(54) BIOFILM GROWTH PREVENTION

(75) Inventor: Steven Kritzler, Cronulla (AU)

(73) Assignee: Novapharm Research (Australia) Pty Ltd, Rosebery, New South Wales (AU)

( * ) Notice: Subject to any disclaimer, the term of this patent is extended or adjusted under 35 U.S.C. 154(b) by 1067 days.

(21) Appl. No.: 10/557,617

(22) PCT Filed: May 18, 2004

(86) PCT No.: PCT/AU2004/000650
§ 371 (c)(1),
(2), (4) Date: Mar. 14, 2006

(87) PCT Pub. No.: WO2004/103071
PCT Pub. Date: Dec. 2, 2004

(65) Prior Publication Data
US 2007/0004596 A1      Jan. 4, 2007

(30) Foreign Application Priority Data

May 21, 2003   (AU) ................................ 2003902552

(51) Int. Cl.
*C09D 5/14*      (2006.01)
(52) U.S. Cl.
USPC ........ 523/122; 424/78.09; 424/405; 523/123; 106/16
(58) Field of Classification Search
USPC ........ 424/78.09; 514/731; 523/122; 106/16
See application file for complete search history.

(56) References Cited

FOREIGN PATENT DOCUMENTS

| AU | 199958339 A1 | | 2/2000 |
|---|---|---|---|
| CA | 2402653 | * | 3/2004 |
| JP | 63 067268 A | | 3/1988 |
| JP | 63 290802 A | | 11/1988 |
| RO | 82572 A | * | 9/1983 |
| WO | 9633748 A1 | | 10/1996 |
| WO | WO 96/33748 | | 10/1996 |
| WO | WO 01/73356 A1 | | 10/2001 |

OTHER PUBLICATIONS

Kritzler, "Biocidal Surface Films", Oct. 31, 1996, International Application Published Under the PCT, WO 96/33748.*
Supplementary European Search Report for corresponding European Patent Application No. 04733513.8-2103/1628528 in the Name of Novapharm Research (Australia) Pty. Limited, Dated Sep. 17, 2010.

* cited by examiner

*Primary Examiner* — Ali Soroush
(74) *Attorney, Agent, or Firm* — Locke Lord LLP

(57) ABSTRACT

A biostatic coating comprising a coating composition which on drying produces an intrinsically hydrophobic film. The coating composition includes a biocidal complex A-B in which A is a phenolic biocide and B is selected from polyvinylpyrrolidone ("PVP"), PVP polymers, PVP copolymers and mixtures thereof. The coating composition for example is selected from acrylic and methacrylic polymer based compositions, acrylic and methacrylic copolymer based compositions, vinyl polymer based compositions, vinyl copolymer based compositions, epoxy resins, epoxy esters, and mixtures thereof. Suitable biocides for use in the invention include, but are not limited to complexes of PVP or PVP copolymer with triclosan; diclosan; dichlorophen; orthophenylphenol; orthobenzylparachlorophenol, cresols, xylols, and substituted diphenyl ethers.

49 Claims, No Drawings

BIOFILM GROWTH PREVENTION

PRIOR RELATED APPLICATIONS

This application is a national stage of amended PCT/AU2004/000650, which has an international filing date of May 18, 2004 and which claims priority to Australian application AU2003902552, filed May 21, 2003. Both applications are incorporated herein in their entirety.

FEDERALLY SPONSORED RESEARCH STATEMENT

Not applicable.

REFERENCE TO MICROFICHE APPENDIX

Not applicable.

FIELD OF THE INVENTION

This invention relates to a method of, and composition for, reduction or prevention of biofilm formation on moist or wet surfaces, and more particularly to the reduction of pathogens in, and in the vicinity of, air-conditioning systems. The invention has been developed primarily for use in air-conditioning (including air cooling and air heating) systems, and will be described hereinafter with reference to this field of use. However, it will be appreciated that the invention can be applied in other situations in which it is desired to inhibit biofilm formation or micro-organism colonization of a surface.

BACKGROUND OF THE INVENTION

Air conditioning systems such as are commonly provided in office, residential, health care and other buildings frequently include components with moist or wet surfaces. A good example is the air conditioner condenser which may comprise a plurality of heat exchange fins, for example of aluminium construction, cooled by heat conductive connection with a recirculating refrigerant. Hot air to be cooled is passed over the fins, and moisture in the air condenses on the fins and drains away. In some cases the heat exchange surfaces of the condenser are cooled by a recirculating thin film of water.

The cooling surfaces are typically of a large area, are moist or wet, and provide an ideal environment for the immobilization and growth of micro-organisms which are carried by the air and which form biofilms on the surfaces. The micro-organisms include bacteria and fungi which multiply on the surface. Within months the space between adjacent heat exchange surfaces may be totally occluded by biofilm growth.

Biofilm reduces efficacy and poses major health risks. Efficacy is lost because the biofilm has poor heat transfer properties and so the thermal efficiency of the condenser is diminished. Microbial activity can also shorten the service life of a system because acidic bacterial exudates can cause serious corrosion and because the increase in biomass on, and in, the components can lessen air-flow and increase back pressure in the system, requiring maintenance cleaning after a short life in service.

The health risk arises because the presence of biofilm in turn provides a haven for the further accumulation and further growth of pathogens such as fungi, bacteria, viruses, allergens, yeasts, and moulds. Conditions for the growth of such organisms are especially favourable during periods of high humidity such as may occur when the system is off, for example at night, but also arise during normal operation. The presence of organisms is highly undesirable because they can cause illness or death in humans and animals, create odours and can damage or destroy a wide variety of materials.

Of particular concern in terms of human health and safety are endotoxins and mycotoxins which are breakdown components of fungal and bacterial cell walls and which are known human respiratory allergens. In some individuals they can trigger asthma attacks, and in all cases have been shown to cause immune response. It is currently thought that over a period of exposure this reduces the ability of the immune system to respond to antagonists and leaves the subject more prone to infection by bacteria, viruses, etc. Also of concern are fungal spores, bacterial spores and bacteria.

In health care facilities such as hospitals and nursing homes the adverse consequences of release of endotoxins and myotoxins from biomass are exacerbated because many of the patients are in a weakened condition due to their primary health care problem. Micro-organisms that would not be a major threat to a healthy person can be fatal to a patient with a diminished capacity to defend themselves from infection. Increasing attention is also being paid to other environments such as public buildings, since if pathogenic micro-organisms find their way via conditioned air or ventilation shafts, into a building they can be rapidly circulated throughout the building thereby greatly increasing the likelihood of the spread of infection and disease. The prevention of spore germination and microbial survival in air conditioning systems would help reduce the risk of illness and hypersensitivity reactions.

To date there has been no effective means of prevention of biomass growth and the only means of addressing the problem has been periodic cleaning, which is labour intensive, costly and inconvenient and which does not adequately deal with health concerns between cleaning operations. Although various coating materials have been proposed, none have been able to resist the moist conditions or remain effective in preventing biofilm formation for a useful period.

It is an object of the present invention to overcome or ameliorate at least one of the deficiencies of the prior art, or to provide a useful alternative.

Many regions of the world employ heated filtered air in buildings as a means of central heating. It will be understood that such systems contribute to the same hazards as described above for air conditioning and the invention is not limited to any particular kind of filter or airflow system.

SUMMARY OF THE INVENTION

According to a first aspect the invention provides a biostatic coating composition comprising a film forming composition which on drying produces an intrinsically hydrophobic film and including a biocidal complex A-B in which A is a phenolic biocide and B is selected from polyvinylpyrrolidone, polyvinylpyrrolidone polymers, polyvinylpyrrolidone copolymers and mixtures thereof, and wherein the biocidal complex A-B is not water soluble.

It will be understood by those skilled in the art that the phrase "not water soluble" means not water soluble at the temperatures at which the composition is used.

Unless the context clearly requires otherwise, throughout the description and the claims, the words 'comprise', 'comprising', and the like are to be construed in an inclusive sense as opposed to an exclusive or exhaustive sense; that is to say, in the sense of "including, but not limited to".

According to a second aspect the invention provides a biostatic coating composition according to the first aspect wherein the coating composition is selected from acrylic polymer based compositions, methacrylic polymer based compositions, acrylic copolymer based compositions, methacrylic copolymer based compositions, vinyl polymer based compositions, vinyl copolymer based compositions, epoxy resins, epoxy esters, and mixtures thereof.

Preferably, the coating composition has bacteriostatic and/or fungistatic properties.

The film forming composition may be based on an emulsion or latex, a polymer or copolymer solution, or a polymer or copolymer emulsion. The film forming composition may be a water-based polymer or copolymer emulsion.

For preference, the film forming composition is or includes an acrylic polymer, acrylic copolymer, mixtures of acrylic polymers, mixtures of acrylic copolymers or mixtures of acrylic polymers and copolymers. More preferably, the film forming composition is or includes an acrylic-styrene copolymer.

The film forming composition may be or includes an epoxy or epoxy ester.

Highly preferred coating compositions are water-based polymers or copolymer emulsion or latex compositions, and especially those including an epoxy ester.

The film forming composition may be or includes a vinyl acetate acrylic copolymer.

Preferably, the film forming composition is present in an amount of 30 to 80% w/w of the mixture, more preferably the film forming composition is present in an amount of 40 to 70% w/w of the mixture and even more preferably the film forming composition is present in an amount of 50 to 60% w/w of the mixture.

Preferred biocides for use in the biocidal complex A-B are triclosan; diclosan; dichlorophen; orthophenylphenol; orthobenzylparachlorophenol, cresols, xylols, and substituted diphenyl ethers.

More preferably, biocide A is a halogenated phenolic biocide, in preference a chloro-phenolic biocide and most preferably, biocide A is triclosan.

Preferably, biocide A is present in an amount of 0.5 to 5% w/w of the mixture, more preferably in an amount of 1 to 2% w/w of the mixture and even more preferably in an amount of 1.5% w/w of the mixture.

Preferably, the complexing partner B is polyvinylpyrrolidone, or may be, for example, a polyvinylpyrrolidone/vinyl acetate copolymer.

Preferably, B is present in an amount of 2 to 10% of the mixture, more preferably B is present in an amount of 3 to 8% of the mixture, and even more preferably B is present in an amount of about 5% of the mixture. Preferably, the biostatic composition contains solvent in an amount of 20 to 40% of the mixture, more preferably 25 to 35% of the mixture. One preferred solvent is water.

It has been practiced to combine a PVP/phenolic complex in a hydrophilic film forming polyvinyl pyrrolidone polymer or copolymer whereby the complex may be loosely bound to impregnated paper or textile wipes for cleaning food preparation surfaces and the like. In the forgoing applications the complex is readily leached from the wipe substrate and can readily contact bacteria on the surface being cleaned/disinfected. The complex does not have any long lasting effect on the surface, and the wipe must be disposed of after approximately a dozen washes. The present applicant was thus surprised to discover that inclusion of the PVP complex in a coating composition applied on, for example, a metal or masonry surface, significantly inhibited biofilm growth on the polymer coated surface, when the coating polymer might have been expected to encapsulate the biocide and protect micro-organisms from contact with the biocide. It was even more surprising that coatings including the complex according to the invention have prevented biomass growth on coated metal for periods exceeding three years in an environment in which such growth was previously a major problem. It is also surprising that such a small concentration of biocide is effective for such a long duration.

It will be appreciated that PVP/phenolic complexes are not water soluble and their inclusion in coating compositions is not simple. This has been achieved in the case of water based emulsion coating compositions by dispersing the complex in the aqueous phase together with a water soluble high boiling point polar solvent (eg N-methyl pyrrolidone or a glycol ether). After the coating is applied, and as the water evaporates, the relative proportion of the high BP polar solvent increases and at a critical point dissolves the biocidal complex leaving the biocide homogeneously distributed throughout the film. It will also be understood that while water is a preferred vehicle, dispersion in solvent based coating compositions can be similarly achieved.

According to a third aspect, the invention provides a biostatic composition according to the first or second aspects further including a water soluble polar solvent having a higher boiling point than a solvent vehicle of the coating composition.

Preferably, the high boiling polar solvent aids dispersion of the complex A-B in a polymer emulsion or latex. Preferably, the water soluble polar solvent is selected from N-methyl pyrrolidone, glycol ethers, and combinations thereof.

Coatings according to the invention may be used as protective coatings on components susceptible to biomass growth, such as air conditioning condenser plates, vents and on other surfaces, eg susceptible surfaces in operating theatres, to prevent the formation of biofilm on the surface. The invention may also be applied in decorative coatings such as paints to prevent mould growth on susceptible surfaces. Coatings according to the invention may be applied (without limitation to surfaces of metal, masonry, timber, particle board, and other building and construction materials). Some compositions may desirably be baked onto the surface or dried at elevated temperatures.

According to a third aspect, the invention provides a biostatic coating formed by drying a film or thin layer of a biostatic coating composition according to any one of the preceding aspects.

The coating is preferably effective to prevent biofilm growth on its surface for in excess of one year, and even more preferably is effective to prevent biofilm growth on its surface for in excess of three years.

The coating may be applied to metal, to concrete or a cementitious surface or to a timber surface.

The coating may be applied in the form of a decorative coating. One example is in the form of a paint to prevent mould growth. Such a paint can further include paint ingredients selected from the group consisting of suspension agents, thixotropic agents, flow and viscosity modifiers, preservatives and the like. Other paint ingredients may be advantageously selected from the group consisting of corrosion inhibitors and/or pigments.

Thus depending on intended end use, compositions according to the invention may be pigmented and in that case will normally include other paint ingredients such as suspension agents, thixotropic agents, flow and viscosity modifiers, preservatives and the like. The compositions need not be pigmented and may include corrosion inhibitors and other additives known to be useful in film-forming coatings.

It will be understood that it is sufficient that the treatment is bacteriostatic or fungistatic. That is to say, it is sufficient that the treating agent stops colonisation on the surface rather than kills organisms on a colonised surface.

According to a fourth aspect, the invention provides a method of inhibiting the formation of a biofilm on a surface susceptible to such formation comprising the steps of applying a coating of a composition according to the first or second aspects to the surface and drying the composition or allowing the composition to dry. In preferred embodiments, the surface is an air conditioning surface, an air conditioning condenser plate, an air conditioning condenser vent, or may be a susceptible surface in an operating theatre.

In some embodiments, the composition is baked onto the surface or dried at elevated temperatures.

According to a fifth aspect, the invention provides a surface treated in accordance with a composition of the first or second aspects or according to a method of the fourth aspect.

DETAILED DESCRIPTION OF THE INVENTION

Following long-standing patent law convention, the terms "a" and "an" mean "one or more" when used in this application, including the claims. Even though the invention has been described with a certain degree of particularity, it is evident that many alternatives, modifications, and variations will be apparent to those skilled in the art in light of the present disclosure. Accordingly, it is intended that all such alternatives, modifications, and variations which fall within the spirit and scope of the invention be embraced by the defined claims.

DESCRIPTION OF EMBODIMENTS OF THE INVENTION

Best Modes for Carrying Out the Invention

Various embodiments of the invention will now be more particularly described by way of example only.

Suitable biocides for use in the invention include, but are not limited to complexes of PVP or PVP copolymer with triclosan; diclosan; dichlorophen; orthophenylphenol; orthobenzylparachlorophenol, cresols, xylols, and substituted diphenyl ethers.

Examples of Formulas

Formulations were prepared as shown in the following examples.

Example 1

| | |
|---|---|
| Styrene/Acrylic Copolymer Emulsion (50% solids) | 60.0% w/w |
| Water | 28.5% w/w |
| N-Methyl Pyrrolidone | 5.0% w/w |
| PVP/VA S-630 | 5.0% w/w |
| Triclosan | 1.5% w/w |

Example 2

| | |
|---|---|
| Acrylic Copolymer Emulsion (50% solids) | 60.0% w/w |
| Water | 28.5% w/w |
| N-Methyl Pyrrolidone | 5.0% w/w |
| PVP/VA S-630 | 5.0% w/w |
| Triclosan | 1.5% w/w |

Example 3

| | |
|---|---|
| Vinyl Acetate/Acrylic Copolymer Emulsion (50% solids) | 60.0% w/w |
| Water | 28.5% w/w |
| N-Methyl Pyrrolidone | 5.0% w/w |
| PVP/VA S-630 | 5.0% w/w |
| Triclosan | 1.5% w/w |

Example 4

| | |
|---|---|
| Acrylic Copolymer Emulsion (50% solids) | 30.0-50.0% w/w |
| Epoxy Resin 1001 | 10.0-20.0% w/w |
| Propylene Glycol Methyl Ether Acetate | 10.0-20.0% w/w |
| PVP/VA S630 | 5.0% w/w |
| 2-Phenoxy Ethanol | 2.0-5.0% w/w |
| Nonyl Phenol Ethoxylate Sulphate Ammonium Salt | 2-3.0% w/w |
| Triclosan | 1.5% w/w |
| Water | qs to 100% w/w |

Example 5

| | |
|---|---|
| Acrylic copolymer (50% active solution in ethanol) | 70% w/w |
| PVP/VA S630 | 5.0% w/w |
| Triclosan | 1.5% w/w |
| Ethanol | 23.5% w/w |

PVP/VA S630 is available from ISP corporation.

A cooling coil in the airconditioning system of a large city building situated in Sydney was thoroughly cleaned and then monitored at intervals over a 12 month period. A significant growth of biomass was observable on the cooling coil within a month, and the coil required cleaning at intervals of approximately 3 months. The coil was then again cleaned and sections of the coil were coated with formulations according to each of examples 1-3. The coil was inspected at intervals. No biofilm growth was observable on the coil after 12 months on any of the coated sections.

The invention claimed is:

1. A water-insoluble biostatic composition suitable for application to surfaces and effective to inhibit biofilm growth for at least 12 months when the surface is moist or wet, the composition comprising:
a film forming combination of a biocidal complex A-B and a film forming water insoluble polymer wherein A of the biocidal complex A-B is a phenolic biocide and B of the biocidal complex A-B comprises a polyvinylpyrrolidone copolymer,
wherein B is selected so that the biocidal complex A-B is not water-soluble but is dispersed in a water-based emulsion by inclusion of a polar solvent or is dispersed in a solvent based vehicle; and wherein the composition dries to a water-insoluble coating when applied to surfaces.

2. A biostatic coating composition according to claim 1 wherein the film forming water insoluble polymer is selected from the group consisting of acrylic polymer based compositions, methacrylic polymer based compositions, acrylic copolymer based compositions, methacrylic copolymer based compositions, vinyl polymer based compositions, vinyl copolymer based compositions, epoxy resins, epoxy esters, and mixtures thereof.

3. A biostatic coating composition according to claim 1 which has bacteriostatic properties.

4. A biostatic coating composition according to claim 1 which has fungistatic properties.

5. A biostatic coating composition according to claim 1 wherein the film forming combination is an emulsion or latex composition.

6. A biostatic coating composition according to claim 1 wherein the film forming combination is a polymer or copolymer solution.

7. A biostatic coating composition according to claim 1 wherein the film forming combination is a polymer or copolymer emulsion.

8. A biostatic coating composition according to claim 7 wherein the film forming combination is a water-based polymer or copolymer emulsion.

9. A biostatic coating composition according to claim 1 wherein the film forming combination is or includes an acrylic polymer or acrylic copolymer.

10. A biostatic coating composition according to claim 1 wherein the film forming combination is or includes an acrylic-styrene copolymer.

11. A biostatic coating composition according to claim 1 wherein the film forming combination is or includes an epoxy or epoxy ester.

12. A biostatic coating composition according to claim 1 wherein the film forming combination includes a vinyl acetate acrylic copolymer.

13. A biostatic coating composition according to claim 1 wherein the film forming combination is present in an amount of 30 to 80% weight/weight (w/w) of the mixture.

14. A biostatic coating composition according to claim 13 wherein the film forming combination is present in an amount of 40 to 70% w/w of the mixture.

15. A biostatic coating composition according to claim 14 wherein the film forming combination is present in an amount of 50 to 60% w/w of the mixture.

16. A biostatic coating composition according to claim 1 wherein biocide A is selected from the group consisting of triclosan, diclosan, dichlorophen, orthophenylphenol, orthobenzylparachlorophenol, cresols, xylols, and substituted diphenyl ethers.

17. A biostatic coating composition according to claim 1 wherein biocide A is a halogenated phenolic biocide.

18. A biostatic coating composition according to claim 16 wherein the biocide A is triclosan.

19. A biostatic coating composition according to claim 1 wherein the biocide A is present in an amount of 0.5 to 5% w/w of the mixture.

20. A biostatic coating composition according to claim 19 wherein biocide A is present in an amount of 1 to 2% w/w of the mixture.

21. A biostatic coating composition according to claim 20 wherein biocide A is present in an amount of 1.5% w/w of the mixture.

22. A biostatic coating composition according to claim 1 wherein B is polyvinylpyrrolidone.

23. A biostatic coating composition according to claim 1 wherein B is polyvinylpyrrolidone/vinyl acetate copolymer.

24. A biostatic coating composition according to claim 1 wherein B is present in an amount of 2 to 10% of the mixture.

25. A biostatic coating composition according to claim 24 wherein B is present in an amount of 3 to 8% of the mixture.

26. A biostatic coating composition according to claim 25 wherein B is present in an amount of about 5% of the mixture.

27. A biostatic coating composition according to claim 1 containing solvent in an amount of 20 to 40% of the mixture.

28. A biostatic coating composition according to claim 27 wherein the solvent is present in an amount of 25 to 35% of the mixture.

29. A biostatic coating composition according to claim 27 wherein the solvent is water.

30. A biostatic coating composition according to claim 27 further including a water soluble polar solvent having a higher boiling point than a solvent vehicle of the coating composition.

31. A biostatic coating composition according to claim 30 wherein the high boiling polar solvent aids dispersion of the complex A-B in a polymer emulsion or latex.

32. A biostatic coating composition according to claim 30 wherein the water soluble polar solvent is selected from the group consisting of N-methyl pyrrolidone, glycol ethers, and combinations thereof.

33. A biostatic coating formed by drying a film or thin layer of a biostatic coating composition on a surface,
    wherein the biostatic coating composition is suitable for application to surfaces and is effective to inhibit biofilm growth on the surface when the surface is moist or wet for at least 12 months;
    wherein the composition dries to a water insoluble coating effective to inhibit biofilm growth on the surface when applied to the surface; and
    wherein the composition comprises a film forming combination of a biocidal complex A-B and a film forming water insoluble polymer wherein A of the biocidal complex A-B is a phenolic biocide and B of the biocidal complex A-B comprises a polyvinylpyrrolidone copolymer, and wherein B is selected so that the biocidal complex A-B is not water soluble but is dispersed in a water based emulsion by inclusion of a polar solvent or is dispersed in a solvent based vehicle.

34. A biostatic coating according to claim 33 which is effective to prevent biofilm growth on its surface for in excess of one year.

35. A biostatic coating according to claim 34 which is effective to prevent biofilm growth on its surface for in excess of three years.

36. A biostatic coating according to claim 33 when applied to metal.

37. A biostatic coating according to claim 33 when applied to concrete or a cementitious surface.

38. A biostatic coating according to claim 33 when applied to a timber surface.

39. A biostatic coating according to claim 33 in the form of a decorative coating.

40. A biostatic coating according to claim 33 in the form of a paint to prevent mould growth.

41. A biostatic coating according to claim 33 in the form of a paint further including paint ingredients selected from the group consisting of suspension agents, thixotropic agents, flow and viscosity modifiers, preservatives and the like.

42. A biostatic coating according to claim 33 in the form of a paint further including as a paint ingredient a corrosion inhibitor.

43. A biostatic coating according to claim 33 in the form of a paint further including a pigment.

44. A method of inhibiting the formation of a biofilm on a surface susceptible to such formation when the surface is moist or wet, the method comprising the steps of:
- applying a coating of a biostatic composition to the surface; and
- drying the biostatic composition or allowing the composition to dry,
- wherein the biostatic composition of the coating comprises a film forming combination of a biocidal complex A-B and a film forming water insoluble polymer wherein A of the biocidal complex A-B is a phenolic biocide and B of the biocidal complex A-B comprises a polyvinylpyrrolidone copolymer, and wherein B is selected so that the biocidal complex A-B is not water soluble but is dispersed in a water based emulsion by inclusion of a polar solvent or is dispersed in a solvent based vehicle, and
- wherein the biostatic composition dries to a water insoluble coating effective to inhibit biofilm growth for at least 12 months on the surface.

45. A method according to claim 44 wherein the surface is an air conditioning surface.

46. A method according to claim 44 wherein the surface is an air conditioning condenser plate.

47. A method according to claim 44 wherein the surface is an air conditioning condenser vent.

48. A method according to claim 44 wherein the surface is a susceptible surface in an operating theatre.

49. A method according to claim 44 wherein the composition is baked onto the surface or dried at elevated temperatures.

* * * * *